United States Patent [19]

Irmscher et al.

[11] Patent Number: 4,590,180
[45] Date of Patent: May 20, 1986

[54] USE OF ADENOSINE DERIVATIVES AS PSYCHOPHARMACOLOGICAL AGENTS

[75] Inventors: Klaus Irmscher; Rochus Jonas, both of Darmstadt; Jürgen Uhl, Seeheim; Ernst Schorscher, Darmstadt, all of Fed. Rep. of Germany

[73] Assignee: Merck Patent Gesellschaft mit beschränkter Haftung, Darmstadt, Fed. Rep. of Germany

[21] Appl. No.: 487,645

[22] Filed: Apr. 22, 1983

Related U.S. Application Data

[63] Continuation-in-part of Ser. No. 265,489, May 20, 1981, abandoned.

[30] Foreign Application Priority Data

May 21, 1980 [DE] Fed. Rep. of Germany ....... 3019322

[51] Int. Cl.$^4$ ...................... A61K 31/70; C07H 19/167
[52] U.S. Cl. ......................................... 514/46; 536/26
[58] Field of Search ...................... 424/180; 536/26; 514/46

[56] References Cited

U.S. PATENT DOCUMENTS

| | | |
|---|---|---|
| 3,472,838 | 10/1969 | Hanessian ........................... 536/26 |
| 3,551,409 | 12/1970 | Kampe et al. ....................... 536/26 |
| 3,838,147 | 9/1974 | Pohlke et al. ....................... 536/26 |
| 3,988,317 | 10/1976 | Kampe et al. ....................... 536/26 |

OTHER PUBLICATIONS

Skolnick et al., "European J. Pharmacol.", 67 (1980) 179–186.
Skolnick et al., "Pharmac. Biochem. Behav.", 12(5) 685–689, 1980.
Skolnick et al., "Life Science", vol. 23, pp. 1473–1480, 1978.

*Primary Examiner*—Johnnie R. Brown
*Attorney, Agent, or Firm*—Millen & White

[57] ABSTRACT

Adenosine derivatives of formula I

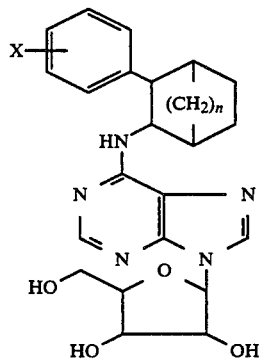

wherein X is F, Cl or Br and n is 1 or 2, and their physiologically acceptable acid addition salts, are valuable psychopharmacological agents.

25 Claims, No Drawings

USE OF ADENOSINE DERIVATIVES AS PSYCHOPHARMACOLOGICAL AGENTS

CROSS REFERENCE TO RELATED APPLICATIONS

This application is a continuation-in-part application of Application Ser. No. 265,489, filed on May 20, 1981, now abandoned.

BACKGROUND OF THE INVENTION

The present invention relates to the use of adenosine derivatives as psychopharmacological agents.

Combating stress conditions, in particular psychic stress conditions, using various psychopharmacological agents is known. Above all, active compounds from the benzodiazepine group, for example diazepam, are used for such purposes. Although these substances are widely used, their administration has certain disadvantages. For example, an increase in appetite, a decrease in libido, menstruation disorders, dizziness and, at high doses, articulation disorders have been observed. Alcohol tolerance is also reduced.

SUMMARY OF THE INVENTION

Accordingly, it is an object of the present invention to provide other compounds which have more favorable properties and which can be used as psychopharmacological agents in the treatment of stress conditions, for example as anxiolytic agents and as tranquilizers.

It is another object of this invention, in particular, to provide such compounds having a structure different from the benzodiazepines and which are well tolerated, do not have the side-effects mentioned, or have them only to a lesser degree.

Upon further study of the specification and appended claims, further objects and advantages of this invention will become apparent to those skilled in the art.

These objects have been achieved in one aspect of this invention by providing a psychopharmacological agent containing a compound of formula I

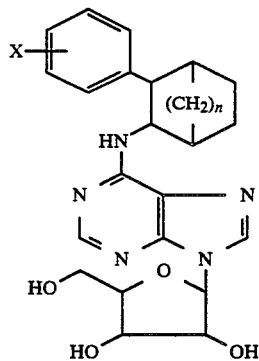

(I)

wherein X is F, Cl or Br and n is 1 or 2, or one of the physiologically acceptable acid addition salts thereof.

In another aspect, this invention relates to the use of such compounds in combating stress conditions in the human or animal body.

The present invention in still another aspect relates to the use of adenosine derivatives of formula I or physiologically acceptable salts thereof for the preparation of psychopharmacological agents, in particular by a non-chemical route. Each of these compounds can be converted into a suitable dosage form together with at least one solid, liquid and/or semi-liquid excipient or auxiliary, and if, desired, in combination with one or more other active compound(s) compatible with the psychopharmacological agent.

The present invention in yet another aspect relates to a psychopharmacological agent, in particular an anxiolytic agent, containing an adenosine derivative of formula I and/or one of its physiologically acceptable salts.

DETAILED DISCUSSION

The compounds of formula I and their pharmacologically acceptable salts are known (compare, for example, German Offenlegungsschriften Nos. 2,117,577 and 2,205,002, both corresponding to U.S. Pat. No. 3,838,147, all of whose disclosures are incorporated by reference herein). Some of their pharmacological actions are also already known, e.g., they cause an increase in coronary flow and an increase in the partial pressure of oxygen in the blood of the coronary veins, and they have an activity in an intravascular pain model and also related actions on the circulation, lipolysis-inhibiting actions and actions which cause lowering of the cholesterol level.

However, it could not be seen from the statements in the literature that the compounds also, and above all, have depressant actions on the central nervous system. This finding is unexpected and surprising.

The compounds of formula I can be prepared, for example, by reacting 6-chloro-, 6-bromo- or 6-methylthio-9-($\beta$-D-ribofuranosyl)-purine with 2-amino-3-X-phenyl-bicyclo[2,2,2]octane or 2-amino-3-X-phenyl-bicyclo[2,2,1]heptane, or by splitting off protective groups from compounds which otherwise correspond to formula I but in which the OH groups are present in the protected form, for example in the etherified or esterified form. Further details are given in the cited German Offenlegungsschrift No. 2,205,002 and U.S. Pat. No. 3,838,147 and in the preparation examples which follow.

The compounds of formula I can be converted into their physiologically acceptable acid addition salts, for example, into their hydrochlorides, hydrobromides, sulfates, nitrates or methanesulfonates, by treatment with the corresponding inorganic or organic acids, preferably strong inorganic or organic acids.

It has been found that the substances of this invention have valuable pharmacological properties, in particular actions on the central nervous system, coupled with a good tolerance. Above all, they have depressant actions on the central nervous system. In detail, they have, in particular, anxiolytic, anticonvulsive and muscle-relaxing properties.

The anxiolytic action can be demonstrated, for example, using an unconditioned conflict test, such as has been described by A. S. Lippa et al. (Pharmacology, Biochemistry, Behavior, Volume 9 (1978) pages 853-856). Thus, for example, in accordance with this method but at a current of 700 $\mu$A, a significant action was observed 30 minutes after intraperitoneal administration of 20 mg/kg of $N^6$-[2-(4-chlorophenyl)-bicyclo[2,2,2]oct-3-yl]-adenosine (Ia; formula I, n=2) to rats, compared with control animals which had only received an injection of a solvent mixture.

The anticonvulsive action can be demonstrated, for example, against spasmogenic and lethal doses of caffeine or pentetrazole to mice and rats. The muscle-relaxing action can be demonstrated, for example, on mice in accordance with the method of Irwin (Psychopharmakologia, Volume 13 (1968) pages 222-257) or on rats in the muscle relaxation pair test [for the method, compare H. Müller-Calgan et al., described in H. P. Zippel (Editor), Memory and Transfer of Information, Plenum Press (New York-London), pages 97-100 (1973)] using a study plan compiled by A. Ribbentrop and W. Schaumann [Arzneimittelforschung, Volume 15, pages 863-868 (1965)]. Anesthesia-potentiating properties, which can be demonstrated, for example, in mice and rats in accordance with the method of Janssen et al. (Journal of Medicinal and Pharmaceutical Chemistry, Volume 1, 1959, pages 281-297), and anesthesia-prolonging actions also occur. The substances furthermore have a tranquilizing action, which can be observed, for example in the spontaneous activity and the threatening behavior of rhesus monkeys [for the method, compare H. Müller-Calgan, Activ. nerv. sup. (Praha), Volume 16, pages 62-64 (1974)].

A sedating action can also be detected on observation of the spontaneous motor activity of mice, the action being detected, for example, with the aid of the following method: groups of 6 mice each are placed in transparent plastic cages and are left in these cages for about 20 minutes in order to adapt to the new environment. The substances are then administered intraperitoneally. The locomotive activity of the animals can be measured with a commercially available apparatus for measuring motility. Intraperitoneal injection of Ia triggers off a dose-dependent decrease in the spontaneous motor activity, and reaches its full extent in the course of 10 minutes. The mice give the impression of being sedated, but react rapidly when touched. After stimulation, the animals appear to revert rapidly to the sedated state. In contrast, animals which receive no injection of Ia exhibit a longer-lasting increase in the locomotive activity after similar stimulation. Ia has a long-lasting action on the spontaneous behavioral activity.

With regard to the anticonvulsive action, a synergistic effect of the compounds of formula I can be observed with benzodiazepines, in particular diazepam. Thus, intraperitoneal administration of sub-effective doses of Ia followed by sub-effective doses of diazepam (that is to say doses which individually still did not exhibit an anticonvulsive effect) produced an anticonvulsive action in mice, the intensity of which depended on the doses of Ia administered. The conventional anticonvulsive protocols mentioned above can be used to demonstrate these effects.

It has furthermore been found that administration of compounds of this invention increases the number of benzodiazepine receptors in the brain of mice. A comparable effect when administering an active compound has not hitherto been observed.

This effect could be demonstrated, for example, as follows: dissolved Ia was administered to general-purpose mice weighing 20-25 g by intraperitoneal injection. For this purpose, the solution of the substance in an aqueous emulsifier mixture was mixed with absolute ethanol in a ratio of 1:1, the mixture was diluted with phosphate-buffered sodium chloride solution in a ratio of 1:10 and the appropriate dose was injected in a volume of at most 0.1 ml. At certain points in time, the animals were decapitated and the "forebrains" were removed and homogenized in 0.32 molar sucrose solution.

The bonding of [$^3$H]-diazepam (tritium-labelled diazepam) to the cell membranes isolated hypotonically from raw synaptosomes was measured in accordance with the method of S. M. Paul and P. Skolnick, (Science, Volume 202 (1978), pages 892-894). Intraperitoneal injection of 30 mg/kg of Ia led to an increase in the bonding of the tritium-labelled diazepam: after 10 minutes, a slight increase could be observed and after between 30 and 240 minutes a significant increase, to the extent of 110-125% of the control, could be observed. A statistically significant increase in the bonding of tritium-labelled diazepam could be observed at doses of between 15 and 60 mg/kg when the bonding was measured 60 minutes after the injection. At a dose of 120 mg/kg, a slight, but statistically significant decrease in the bonding of [$^3$H]-diazepam was observed. When a Scatchard evaluation method was applied to the results of a typical experiment (45 mg/kg, administered 30 minutes *before* decapitation), it was found that the increase in [$^3$H]-diazepam bonding is to be attributed to an increase in the number of benzodiazepine receptors and not to a change in the apparent affinity.

As a result of this effect on the benzodiazepine receptors, the compounds of this invention can be used to potentiate the CNS-depressant activity of benzodiazepines in general, especially diazepam.

The psychopharmacological agents of this invention can be used as medicaments in human medicine or veterinary medicine. Suitable excipients include organic or inorganic substances which are suitable for enteral (for example oral) or parenteral administration or topical application and which do not react with the compounds of formula I, for example water, vegetable oils, benzyl alcohols, polyethylene glycols, glycerol triacetate, gelatin, carbohydrates, such as lactose or starch, magnesium stearate and talc. Tablets, dragees, capsules, syrups, elixirs or drops are used, in particular, for oral application, suppositories are used for rectal administration and solutions, preferably oily or aqueous solutions, and furthermore suspensions, emulsions or implants are used for parenteral administration. The compounds can also be lyophilized, and the resulting lyophilizates can be used, for example, for the preparation of injection formulations. The formulations mentioned can be sterilized and/or can contain auxiliaries, such as lubricants, preservatives, stabilizers and/or wetting agents, emulsifiers, salts for influencing the osmotic pressure, buffer substances, colorants, flavoring substances and/or aroma generating substances. If desired, they can also contain one or more other active compounds, for example one or more vitamins and/or one or more other psychopharmacologically active substances, in particular benzodiazepines.

The present invention also relates to the use of an adenosine derivative of this invention in combating stress conditions, in particular psychic stress conditions (of an endogenic or exogenic origin) in the human or animal body, in particular excitation, tension, anxiety, psychoneurotic disorders, autonomic dystonia, psychosomatic disorders (in particular of the heart, circulation, stomach or intestines), sleep disorders, muscular tension (also in cases of rheumatism), spasms and status epilepticus, and also to facilitate birth and during surgical intervention, and to their use in therapeutic treatment of the human or animal body.

The adenosine derivatives of this invention are as a rule administered analogously to known commercially available psychopharmacological agents, for example diazepam, and preferably in dosages of about 10 to 1,000 mg, in particular of 60 to 300 mg and above all of 150 to 200 mg, per dosage unit. The daily dosage is preferably about 0.2 to 20 mg/kg of body weight. However, the specific dose for each particular patient depends on the usual highly diverse factors, for example on the activity of the particular compound employed, on the age, body weight, general state of health, sex and diet of the patient, on the point in time and method of administration, on the rate of elimination, on the medicament combination and on the severity of the particular illness to which therapy applies. Oral administration is preferred.

A determination of a satisfactory dosage of a compound of this invention to achieve a particular CNS-depressant action to treat a particular indication can be accomplished by conventional procedures, e.g., including a comparison of the relative activity of the compound of this invention with that of an analogous known CNS-depressant such as diazepam using a conventional pharmacological protocol for the given indication such as those mentioned above.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following examples, all temperatures are set forth uncorrected in degrees Celsius; unless otherwise indicated, all parts and percentages are by weight.

Preparation examples

EXAMPLE 1

A mixture of 28.6 g of 6-chloro-9($\beta$-D-ribofuranosyl)-purine, 23.6 g of 2-amino-3-p-chlorophenylbicyclo[2,2,2]octane, 450 ml of dimethylformamide, 450 ml of isopropanol and 50 ml of triethylamine is left to stand at 20° for 4 days. The mixture is evaporated, the residue is dissolved in chloroform, the chloroform solution is washed with 1% aqueous acetic acid and evaporated again and the residue is triturated with ether to give $N^6$-[2-(4-chlorophenyl)-bicyclo[2,2,2]oct-3-yl]-adenosine (Ia). M.p.: 145° (decomposition). Rf: 0.41 (silica gel; $CH_2Cl_2:CH_3OH$ 9:1).

EXAMPLE 2

Analogously to Example 1, equimolar amounts of 6-bromo-9-($\beta$-D-ribofuranosyl)-purine and 2-amino-3-p-chlorophenyl-bicyclo[2,2,1]-heptane give $N^6$-[2-(4-chlorophenyl)-bicyclo[2,2,1]hept-3-yl]-adenosine (Ib). M.p.: 145° (decomposition). Rf: 0.43 (silica gel; $CH_2Cl_2:CH_3OH$ 9:1).

EXAMPLE 3

72 g of $N^6$-(2-p-chlorophenyl-bicyclo[2,2,2]oct-3-yl)-2',3',5'-tri-O-acetyl-adenosine (obtainable from 1-(tri-O-acetyl-$\beta$-D-ribofuranosyl)-6-chloro-purine and 2-amino-3-p-chlorophenylbicyclo[2,2,2]octane in isopropanol) is boiled with a solution of 1 g of sodium in 1 l of methanol for 90 minutes. The mixture is then neutralized with acetic acid and evaporated and the residue is chromatographed on 700 g of silica gel (chloroform:methanol 99:1). Ia is obtained.

EXAMPLE 4

(a) 1 g of $N^6$-(2-p-chlorophenyl-bicyclo[2,2,1]hept-3-yl)-adenosine is boiled with 10 ml of hexamethyl-disilazane for 15 hours and the mixture is then evaporated and the residue is left to stand with 1.6 g of 2,3,5-tri-O-benzyl-D-ribofuranosyl chloride in 50 ml of acetonitrile at 20° for 3 days. The mixture is then boiled for 2 hours. The solvent is evaporated off and the residue is partitioned between water and chloroform. 2',3',5'-tri-O-benzyl-$N^6$-(2-p-chlorophenyl-bicyclo-[2,2,1]hept-3-yl)-adenosine is obtained as an amorphous syrup from the chloroform layer.

(b) The resulting crude product is taken up in 50 ml of ethanol and hydrogenated on 0.5 g of palladium-on-charcoal at 20°, while shaking. The catalyst is filtered off and the filtrate is evaporated to give Ib.

The examples which follow relate to pharmaceutical formulations which contain compounds of the formula I or their physiologically acceptable salts:

EXAMPLE A: Tablets

A mixture of 1.5 kg of Ia, 6 kg of lactose, 1.8 kg of potato starch, 0.3 kg of talc and 0.15 kg of magnesium stearate is pressed into tablets in the customary manner, such that each tablet contains 150 mg of active compound.

EXAMPLE B: Dragees

Tablets are pressed in a manner analogous to that in Example A, and are then covered in the customary manner with a coating of sucrose, potato starch, talc, tragacanth and colorant.

EXAMPLE C: Capsules

Hard gelatin capsules are filled with 3 kg of Ib in the customary manner, such that each capsule contains 300 mg of active compound.

EXAMPLE D: Ampoules

A solution of 1 kg of Ia in 30 l of doubly distilled water is filtered under sterile conditions and ampoules are filled with the solution, the solution is lyophilized under sterile conditions and the ampoules are sealed under sterile conditions. Each ampoule contains 50 mg of active compound.

EXAMPLE E

The procedures of Examples A–D are repeated using pharmacologically acceptable salts of Ia or Ib in place of the compound of formula I.

EXAMPLE AA

The compounds of this invention can be administered to patients, e.g., humans, suffering from any of the foregoing indications or other related indications such as those for which diazepam (Valium) is conventionally administered. Appropriate dosages can be conventionally determined as indicated above. Determination of treatment duration and general regimen is by conventional considerations such as those used in conjunction with diazepam therapy taking into account the differences in potency and other actions involved in each case.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A method of achieving a CNS-depressant effect in a patient suffering from an indication which can be treated by achieving such an effect, which comprises administering to such a patient an amount of a compound of the formula

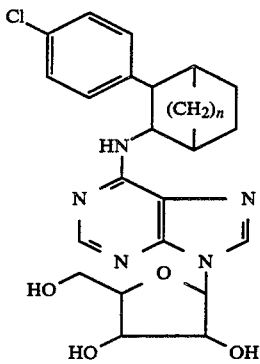

wherein n is 1 or 2 or a physiologically acceptable acid addition salt thereof, effective to achieve said CNS-depressant effect in the patient which relieves the indication.

2. A method of claim 1 wherein the amount of the compound administered is 0.2 to 20 mg/kg/day in unit doses of 10–1,000 mg.

3. A method of claim 2 wherein the administration is oral.

4. A method of claim 1 wherein the indication is a stress condition of endogenic or exogenic origin.

5. A method of claim 4 wherein the CNS-depressant effect is an anxiolytic, tranquilizing, anticonvulsive, muscle relaxing, sedative, anesthesia-potentiating or anesthesia-prolonging effect.

6. A method of claim 5 wherein the CNS depressant effect is an anxiolytic effect.

7. A method of claim 5 wherein the CNS-depressant effect is a tranquilizing effect.

8. A method of claim 5 wherein the CNS-depressant effect is an anticonvulsive effect.

9. A method of claim 5 wherein the CNS-depressant effect is a muscle relaxing effect.

10. A method of claim 5 wherein the indication is a stress condition with an attendant symptom of excitation, tension, anxiety, a psychoneurotic disorder, autonomic dystonia, a psychosomatic disorder, a sleep disorder, muscular tension, spasms or status epilepticus.

11. A method of claim 1 wherein the patient is not suffering from a condition which is treatable by administering a pharmaceutical which influences the transport of oxygen in the blood or affects the lipid metabolism.

12. A method of claim 11 wherein the patient is not suffering from angina pectoris, arteriosclerosis or hyperlipidemia.

13. A method of claim 8 which additionally comprises simultaneously administering a benzodiazepine having CNS-depressant activity.

14. A pharmaceutical composition consisting essentially of an amount of a benzodiazepine having CNS-depressant activity and an amount of an adenosine derivative of the formula

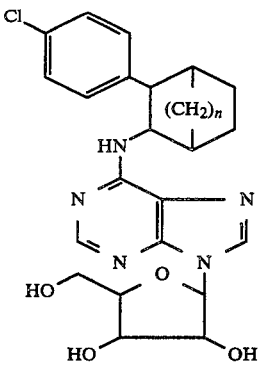

wherein n is 1 or 2 or a physiologically acceptable acid addition salt thereof, these amounts together being effective to achieve anti-convulsant effects in a patient, and a pharmaceutically acceptable adjuvant.

15. A method of potentiating the CNS-depressant activity of a benzodiazepine which comprises simultaneously administering a compound of the formula

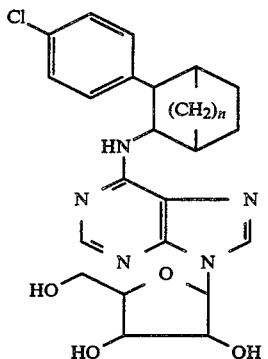

wherein n is 1 or 2 or a physiologically acceptable acid addition salt thereof, and a benzodiazepine.

16. A pharmaceutical composition consisting essentially of an amount of a compound of the formula

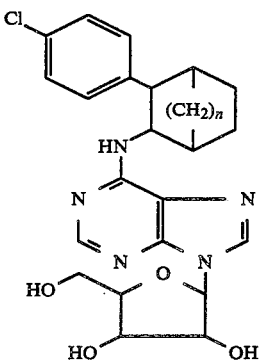

wherein n is 1 or 2 or a physiologically acceptable acid addition salt thereof, effective to potentiate the CNS-depressant activity of a benzodiazepine, and an amount of a benzodiazepine, the total amount of both ingredients being effective to achieve a CNS-depressant effect.

17. A method of achieving a psychopharmacological effect in a human patient comprising administering to the patient an amount of a compound of the formula

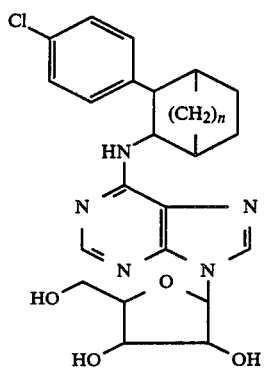

wherein n is 1 or 2 or a physiologically acceptable acid addition salt thereof, effective to achieve a psychopharmacological effect.

18. A method of claim 5 wherein the CNS-depressant effect is a sedative effect.

19. A method of increasing the number of benzodiazepine receptors in the brain of a patient comprising administering to the patient an amount of a compound of the formula

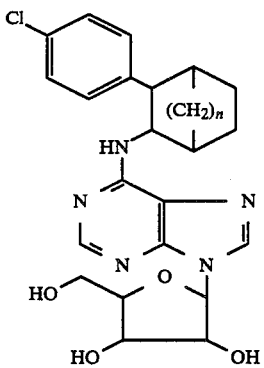

wherein n is 1 or 2 or a physiologically acceptable acid addition salt thereof, effective to increase the number of benzodiazepine receptors in the patient's brain.

20. A method of achieving a CNS-depressant effect in a patient suffering from an indication which can be treated by achieving such an effect, which comprises administering to such a patient an amount of a compound of the formula

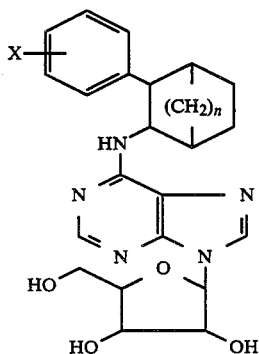

wherein X is F, Br, o-Cl or m-Cl and n is 1 or 2 or a physiologically acceptable acid addition salt thereof, effective to achieve said CNS-depressant effect in the patient which relieves the indication.

21. A pharmaceutical composition consisting essentially of an amount of a benzodiazepine having CNS-depressant activity and an amount of an adenosine derivative of the formula

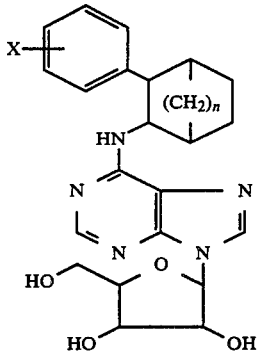

wherein X is F, Br, o-Cl or m-Cl and n is 1 or 2 or a physiologically acceptable acid addition salt thereof, these amounts together being effective to achieve anticonvulsant effects in a patient, and a pharmaceutically acceptable adjuvant.

22. A method of potentiating the CNS-depressant activity of a benzodiazepine which comprises simultaneously administering a compound of the formula

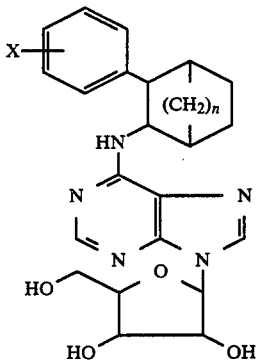

wherein X is F, Br, o-Cl or m-Cl and n is 1 or 2 or a physiologically acceptable acid addition salt thereof, and a benzodiazepine.

23. A pharmaceutical composition consisting essentially of an amount of a compound of the formula

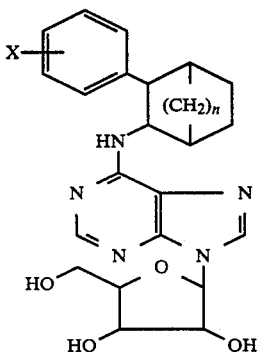

wherein X is F, Br, o-Cl or m-Cl and n is 1 or 2 or a physiologically acceptable acid addition salt thereof, effective to potentiate the CNS-depressant activity of a benzodiazepine, and an amount of a benzodiazepine, the total amount of both ingredients being effective to achieve a CNS-depressant effect.

24. A method of achieving a psychopharmacological effect in a human patient comprising administering to the patient an amount of a compound of the formula

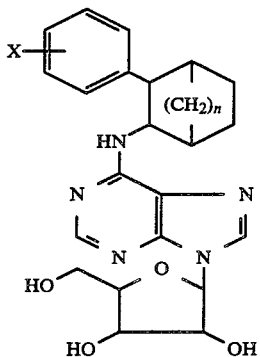

wherein X is F, Br, o-Cl or m-Cl and n is 1 or 2 or a physiologically acceptable acid addition salt thereof, effective to achieve a psychopharmacological effect.

25. A method of increasing the number of benzodiazepine receptors in the brain of a patient comprising administering to the patient an amount of a compound of the formula

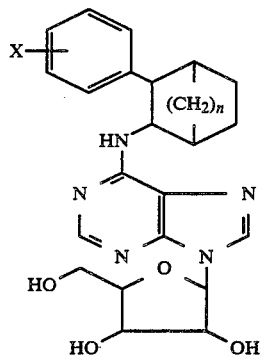

wherein X is F, Br, o-Cl or m-Cl and n is 1 or 2 or a physiologically acceptable acid addition salt thereof, effective to increase the number of benzodiazepine receptors in the patient's brain.

* * * * *